United States Patent [19]

Locatell et al.

[11] Patent Number: 5,149,830
[45] Date of Patent: Sep. 22, 1992

[54] SUBSTITUTED XANTHENE COMPOUNDS

[75] Inventors: Louis Locatell, Chico, Calif.; Kenneth Norland, Lexington, Mass.; F. Donald Roberts, Dover, Mass.; Charles Zepp, Berlin, Mass.

[73] Assignee: Steadfast, Inc., Cambridge, Mass.

[21] Appl. No.: 484,429

[22] Filed: Feb. 23, 1990

[51] Int. Cl.⁵ .............. G03C 1/40; G03C 1/84; G03C 5/54; G03C 1/10
[52] U.S. Cl. .................. 549/223; 549/226; 549/390
[58] Field of Search ......... 549/223, 226, 388, 389, 549/390

[56] References Cited

U.S. PATENT DOCUMENTS

| | | | |
|---|---|---|---|
| 3,100,207 | 8/1963 | Zirkle | 549/388 |
| 4,268,514 | 5/1981 | Galt et al. | 549/388 |
| 4,304,834 | 12/1981 | Cournoyer et al. | 549/388 |
| 4,681,950 | 7/1987 | Fischer et al. | 549/388 |

Primary Examiner—Kriellion S. Morgan
Attorney, Agent, or Firm—Wolf, Greenfield & Sacks

[57] ABSTRACT

Substituted xanthene compounds are described which are capable of functioning as absorbers in high intensity light protective compositions and in materials used to prevent the transmission of high intensity light at selected wavelengths. Also described are high intensity light protective compositions containing an effective amount of a substituted xanthene compound and a polymeric compound and a material which prevents transmission of high intensity light at wavelengths between about 482 to about 556 nanometers. The material of this invention can be used to make protective eyewear, optical filters, shields for protecting a persons body from high intensity light, or shields for protecting components of an optical instrument from high intensity light.

14 Claims, 1 Drawing Sheet

SUBSTITUTED XANTHENE COMPOUNDS

BACKGROUND

The use of high intensity light, e.g. lasers, is becoming more prevalent in various fields. For example, lasers are frequently used in medical and military applications.

Protective equipment is often necessary to prevent a person or objects from being harmed by high intensity light. Laser light, for example, can be very intense and is capable of damaging a person's eyesight. The intensity of the light can be amplified by the cornea onto the retina thereby damaging the eyes. In some cases, objects such as photocells or other equipment can be damaged by exposure to high intensity light.

Presently available means for protecting a person from laser light include protective equipment having a phthalocyanine dye incorporated within the object or diffraction gratings spaced specifically to absorb various wavelengths of light. The devices having diffraction gratings are often difficult and expensive to manufacture The diffraction grating devices can also have reduced efficiency when light is being transmitted at an angle other than 90 degrees.

SUMMARY

This invention pertains to substituted xanthene compounds capable of functioning as absorbers in high intensity light protective compositions and materials used to prevent the transmission of high intensity light at selected wavelengths. Laser light is a source of high intensity light which can be shielded by use of this invention. The substituted xanthene compounds of this invention have the following formula:

The $R_1$—$R_6$ moieties are each independently alkyl, alkenyl, alkynyl, halogen, haloalkyl, —$SO_2N(alkyl)_2$, aryl, substituted aryl, or hydrogen. The $Y_1$ and $Y_2$ moieties are each independently alkyl, alkenyl, alkynyl, or hydrogen. The $X_1$, $X_2$, $X_3$, and $X_4$ moieties are each independently selected from the group consisting of hydrogen, halogen, haloalkyl, alkyl, alkenyl, alkynyl, $NO_2$, SO, $SO_2N(alkyl)_2$, or $SO_2$. The pendant Z moiety attached to the heterocylic ring of the xanthene core is selected from the group consisting of phenyl, substituted phenyl, and hydrogen.

In the compounds of this invention, at least two of the $R_1$—$R_6$ moieties are not hydrogen. Also, naphthyl moieties can be attached to the nitrogen atoms because the $R_3$ or $R_4$ moieties can optionally form a phenyl ring with the $R_5$ moiety or the $R_1$ or $R_2$ moieties can optionally form a phenyl ring with the $R_6$ moiety.

The preferred subgenus of substituted xanthene compounds of this invention are of the formula:

wherein $Y_1$, $Y_2$, $R_5$, and $R_6$ hydrogen; $X_1$, $X_2$, $X_3$, and $X_4$ are each independently halogen, hydrogen or alkyl; $R_1$, $R_2$, $R_3$, and $R_4$ are homologous lower alkyl groups; and A is selected from the group consisting of —$SO_3$, —$SO_2N(alkyl)_2$, $CO_2$, and —$CO_2CH_3$.

This invention also pertains to high intensity light protective compositions containing an effective amount of a substituted xanthene compound and a polymeric compound. The composition can also have a combination of substituted xanthene compounds or a combination of a substituted xanthene compound(s) with at least one other absorber known to absorb light at a particular wavelength. The preferred high intensity light to be shielded is laser light and the preferred substituted xanthene compounds used in the high intensity light protective compositions are those depicted above in formula I. The polymeric compound is a material capable of being used for high intensity light protective purposes. Examples of such compounds include polymeric compositions, plastic and glass.

This invention further pertains to a material which prevents transmission of high intensity light at wavelengths between about 482 to about 556 nanometers. The material of this invention can be used to make protective eyewear, optical filters, shields for protecting a person's body from the high intensity light, or shields for protecting components of an optical instrument from high intensity light. The material carries an effective amount of a substituted xanthene compound, the preferred substituted xanthene compound being that depicted in formula I.

This invention further pertains to a method for solubilizing an absorber in a solvent by admixing the absorber with a surface active quaternary ammonium compound. The preferred absorber is a substituted xanthene compound and the preferred quaternary ammonium compound is dimethyldioctadecylammonium chloride.

The invention further relates to a method for quenching fluorescence in a material by introducing phosphotungstic or phosphomolybdic acid into the material.

The phosphotungstic or phosphomolybdic acid is preferably introduced with an absorber. The preferred absorber is a substituted xanthene compound and the preferred additive is phosphotungstic acid. The phosphotungstic or phosphomolybdic acid also may also enhance the thermal stability of the absorber in the material.

It is an object of the invention to provide a substituted xanthene compound capable of blocking or absorbing high intensity light at selected wavelengths while providing for a substantial amount of other light to transmit through the material.

Another object of the invention is to provide materials and methods for forming protective equipment carrying an absorber, e.g., glasses, goggles, or shields for both people and optical instruments.

Another object is to provide a protective material which can be used for a relatively long time without the addition of more absorber.

Yet another object of the invention is to provide a substituted xanthene compound having improved high intensity light protective properties when compared to known absorbers.

Still another object of the invention is to provide means and methods for solubilizing absorbers such as aromatic dyes.

Still another object of the invention is to provide means and methods for quenching fluorescence in a material.

DETAILED DESCRIPTION

This invention pertains to substituted xanthene compounds of the formula:

wherein $R_1$–$R_6$ are each independently alkyl, alkenyl, alkynyl, halogen, haloalkyl, —$SO_2N(alkyl)_2$, aryl, substituted aryl, or hydrogen; $Y_1$ and $Y_2$ are each independently alkyl, alkenyl, alkynyl, or hydrogen; $X_1$, $X_2$, $X_3$ and $X_4$ are each independently selected from the group consisting of hydrogen, halogen, haloalkyl, alkyl, alkenyl, alkynyl groups $NO_2$, SO, $SO_2N(alkyl)_2$ or $SO_2$; and Z is selected from the group consisting of hydrogen, phenyl and substituted phenyl. At least two of the $R_1$–$R_6$ moieties of the substituted xanthene compounds of the present invention are not hydrogen. Further, naphthyl moieties can be attached to the nitrogens atoms because the $R_3$ or $R_4$ moieties can optionally form a phenyl ring with the $R_5$ moiety or the $R_1$ or $R_2$ moieties can optionally form a phenyl ring with the $R_6$ moiety.

The preferred subgenus of substituted xanthene compounds of this invention are of the formula:

wherein $Y_1$, $Y_2$, $R_5$, $R_6$, $X_3$ and $X_4$ are hydrogen; $X_1$ and $X_2$ are halogen, hydrogen or alkyl; $R_1$, $R_2$, $R_3$, and $R_4$ are the same lower alkyl group; and A is selected from the group consisting of —$SO_3$, —$SO_2N(alkyl)_2$, $CO_2$, and —$CO_2CH_3$.

The term substituted xanthene compound for purposes of this invention is intended to include the compounds and salts thereof. The salts include sodium, potassium and halogen salts, e.g. chloride, bromide or fluoride. The substituted xanthene compounds of this invention are useful as absorbers. The term absorber is intended to encompass compounds capable of absorbing light at particular wavelengths. It should be understood that the substituted xanthene compounds are also dyes because they impart a color. The term absorber is also intended to encompass dyes for purposes of this invention.

The terms alkyl, alkenyl, and alkynyl are intended to include branched or straight chained alkyl, alkenyl or alkynyl groups, and preferably lower alkyl, alkenyl, or alkynyl groups having from 1 to 6 carbon atoms. Example of such lower alkyl groups include methyl, ethyl, ethenyl, ethynyl, propyl, propenyl, or propynyl the most preferred being lower alkyl groups, particularly methyl.

The term halogen is art recognized and is intended to encompass the elements listed in Group VII of the periodic table. Examples of halogens include Cl, Br, F, and I.

The term haloalkyl is intended to include alkyl groups wherein at least one of the hydrogen atom is replaced with a halogen substituent. Examples of haloalkyls include $CF_3$, $-CHF_2$, $-CH_2F$, $-CCl_3$, $-CHCl_2$, and $-CH_2Cl$.

The term substituted phenyl includes phenyl groups substituted with a carboxylate, sulfonate, phosphonate or derivatives thereof. The term derivative can include compounds which are structurally similar such as esters and amides. Examples of such substituted phenyls include those having the formula wherein A is selected from the group consisting $SO_2N\text{-}(alkyl)_2$, $CO_2$, and $CO_2CH_3$.

The term substituted aryl includes aryl group substituted with groups such as alkyl, alkenyl, alkynyl, halogen, or haloalkyl groups. These substituents are as defined above.

The substituted xanthene compounds of this invention preferably have R and X groups positioned such that the overall compound is optically symmetrical. For purposes of this invention optically symmetrical compounds are those compounds wherein the substituents on the phenyl rings are positioned in an identical fashion and the substituents on the phenyl rings of the xanthene core are also positioned identically. For example, the compound is considered to be symmetrical when the $R_1$, $R_2$, $R_3$, and $R_4$ moieties are located in either the 2,6 or 3,5 positions of the phenyl rings and $X_3$ and $X_4$ are located in the 2, 7 or 1, 8 positions on the xanthene core as depicted below.

The preferred optically symmetrical compounds are those in which the corresponding moieties on the phenyl rings are homologous to each other and the most preferred compounds are those in which the corresponding moieties are the safe. For example, in the above depicted compounds $R_1$ is homologous with $R_3$, $R_2$ is homologous with $R_4$, $R_6$ is homologous with $R_5$, $X_1$ is homologous with $X_2$, and $X_3$ is homologous with $X_4$. The term homologous is intended to encompass homologous and substantially homologous moieties. Substantially homologous moieties are those moieties having either the same number of carbon atoms or differ in only a small number of carbon atoms. For example, methyl and butyl moieties are considered to be substantially homologous.

The preferred species of absorbers or xanthene compounds are set forth in Table I below, the most preferred absorber being number 3. The substituted xanthene compounds set forth in Table I are either a salt formed with M, a mixture with M or are in association with M. M is selected from the group consisting of phosphotungtic acid (PT), chloride (Cl) or phosphomolybdic acid (PM). When referring to the absorber by number within this application, e.g. absorber 3, this is meant to be both the compound and M if an M is listed in Table I for the particular absorber.

TABLE I

| Absorber | M | $R_1$ | $R_2$ | $R_3$ | $R_4$ | $R_5$ | $R_6$ | $Y_1$ | $Y_2$ | $X_1$ | $X_2$ | $X_3$ | $X_4$ | Z |
|---|---|---|---|---|---|---|---|---|---|---|---|---|---|---|
| 1 | — | $CH_3$ | $CH_3$ | $CH_3$ | $CH_3$ | H | H | H | H | H | H | H | H | $SO_3$-phenyl |
| 2 | — | $CH_3$ | $CH_3$ | $CH_3$ | $CH_3$ | H | H | H | H | Cl | Cl | H | H | " |
| 3 | PT | $CH_3$ | $CH_3$ | $CH_3$ | $CH_3$ | H | H | H | H | Cl | Cl | H | H | " |
| 4 | — | $CH_3$ | $CH_3$ | $CH_3$ | $CH_3$ | H | H | H | H | H | H | H | H | $SO_2N(CH_3)_2$-phenyl |
| 5 | PT | $CH_3$ | $CH_3$ | $CH_3$ | $CH_3$ | H | H | H | H | H | H | H | H | " |
| 6 | PT | $CH_3$ | $CH_3$ | $CH_3$ | $CH_3$ | H | H | H | H | H | H | H | H | $CO_2$-phenyl |
| 7 | Cl | $CH_3$ | $CH_3$ | $CH_3$ | $CH_3$ | H | H | H | H | H | H | H | H | $CO_2Me$-phenyl |
| 8 | PT | $CH_3$ | $CH_3$ | $CH_3$ | $CH_3$ | H | H | H | H | H | H | H | H | " |
| 9 | PM | $CH_3$ | $CH_3$ | $CH_3$ | $CH_3$ | H | H | H | H | H | H | H | H | " |
| 10 | — | Cl | $CH_3$ | Cl | $CH_3$ | H | H | H | H | H | H | H | H | $SO_3$-phenyl |
| 11 | — | Cl | Cl | Cl | Cl | H | H | H | H | H | H | H | H | " |
| 12 | — | sec$C_4H_9$ | H | sec$C_4H_9$ | H | H | H | H | H | H | H | H | H | " |
| 13 | — | $C_2H_5$ | $C_2H_5$ | $C_2H_5$ | $C_2H_5$ | H | H | H | H | H | H | H | H | " |

TABLE I-continued

| Absorber | M | $R_1$ | $R_2$ | $R_3$ | $R_4$ | $R_5$ | $R_6$ | $Y_1$ | $Y_2$ | $X_1$ | $X_2$ | $X_3$ | $X_4$ | Z |
|---|---|---|---|---|---|---|---|---|---|---|---|---|---|---|
| 14 | — | i-$C_3H_7$ | i-$C_3H_7$ | i-$C_3H_7$ | i-$C_3H_7$ | H | H | H | H | H | H | H | H | $SO_3$-Ph |
| 15 | — | $CH_3$ | $CH_3$ | $CH_3$ | $CH_3$ | H | H | H | H | H | H | $nC_6H_{13}$ | $nC_6H_{13}$ | " |
| 16 | — | $CH_3$ | $CH_3$ | $CH_3$ | $CH_3$ | H | H | H | H | Cl | Cl | $nC_6H_{13}$ | $nC_6H_{13}$ | " |
| 17 | — | $CH_3$ | $CH_3$ | $CH_3$ | $CH_3$ | $CH_3$ | $CH_3$ | H | H | H | H | H | H | " |
| 18 | — | $CF_3$ | H | $CF_3$ | H | H | H | H | H | H | H | H | H | " |
| 19 | — | $CH_3$ | $CH_3$ | $CH_3$ | $CH_3$ | $SO_2N(C_4H_9)_2$ | $SO_2N(C_4H_9)_2$ | H | H | H | H | H | H | " |
| 20 | PT | $C_3H_6$ | $C_4H_8$ | $C_3H_6$ | $C_4H_8$ | H | H | H | H | Br | Br | H | H | " |
| 21 | — | $C_4H_7$ | $C_3H_6$ | $C_3H_7$ | $C_3H_6$ | H | H | $CH_3$ | $CH_3$ | Cl | Cl | H | H | " |
| 22 | PT | Cl | $CH_3$ | Cl | $CH_3$ | $CH_3$ | $CH_3$ | H | H | H | H | H | H | " |
| 23 | — | $C_4H_6$ | $CH_3$ | $C_4H_6$ | $CH_3$ | H | H | H | H | F | F | H | H | " |
| 24 | PM | $CH_3$ | $CH_3$ | $CH_3$ | $CH_3$ | H | H | H | H | $CF_3$ | $CF_3$ | H | H | $CO_2$-Ph |
| 25 | — | $C_2H_5$ | $C_2H_5$ | $C_2H_5$ | $C_2H_5$ | H | H | H | H | H | H | $CF_3$ | $CF_3$ | Ph |
| 26 | PT | Cl | Cl | Cl | Cl | H | H | H | H | $CH_3$ | $CH_3$ | $CH_3$ | $CH_3$ | " |
| 27 | — | $CF_3$ | $CH_3$ | $CH_3$ | $CH_3$ | H | H | H | H | Cl | Cl | $CH_3$ | $CH_3$ | $CO_2$-Ph |
| 28 | — | $CH_3$ | $CH_3$ | $CH_3$ | $CH_3$ | H | H | H | H | H | H | Cl | Cl | $SO_3$-Ph |
| 29 | PT | $CH_3$ | $CH_3$ | $CH_3$ | $CH_3$ | H | H | H | H | H | H | Cl | Cl | " |

Methods for Preparing Substituted Xanthene Compounds

The substituted xanthene compounds of this invention can be prepared by first reacting a compound of the following formula:

(II)

wherein A and B are leaving groups, e.g. halogen, $X_3$ and $X_4$ are as defined earlier, and Z is hydrogen, phenyl, or substituted phenyl, with a substituted aniline or mixture of two different substituted anilines of the formula:

(III)

wherein $R_1$–$R_6$ are each independently alkyl, alkenyl, alkynyl, halogen, haloalkyl, —$SO_2N(alkyl)_2$, aryl, substituted aryl, or hydrogen and $Y_1$ and $Y_2$ are each independently alkyl, alkenyl, alkynyl, or hydrogen. The intermediates formed during this first step have the following formula:

(IV)

wherein A and B are hydroxyl or chloro and $X_3$ and $X_4$ are as defined earlier.

The starting materials can be prepared using conventional techniques known in the art. For example, a benzene ring substituted with, e.g. hydroxyl or chloro groups, can be reacted with an ortho substituted carboxybenzene sulfonic acid forming the xanthene core of the starting material. The reaction is preferably conducted by heating in the presence an acid for about five hours at a temperature of about 155° C. The product is preferably purified using conventional techniques. For example, the product can be filtered, washed in water followed by dissolution in hot water/NaOH. This solution is filtered through glass wool and acidified. The solid is then filtered, washed in water followed by a wash in acetone. The hydroxyl groups can be converted to halogens using conventional halogenating agents, e.g. thionyl chloride/dimethyl formamide in ethyl acetate, $PCl_5$, $PCl_3$, $SO_2CL_2$, $SOCl_2$, and $SOBr_2$.

This invention also pertains to novel starting materials having the formula depicted below:

Wherein $X_1$–$X_4$ are each independently selected from the group consisting of OH, Cl, and n—$C_6H_{13}$. Some of the species are as follows:

wherein the R, Y, X, and Z moieties are as defined for formula I.

The reaction is conducted at a temperature which allows the reaction to occur, preferably between 170°–220° C. using an excess of the substituted aniline reagent. Preferably, twelve moles of the substituted aniline compound is used for each mole of the compound of formula II. The reaction is preferably carried out in the presence of a solvent and optionally a base. The substituted aniline(s) can be dissolved in a polyether or ether-alcohol solvent, e.g. 2-methoxyethanol, diethylene glycol or ethylene glycol. Examples of bases that can be added to the solvent include powdered potassium hydroxide, sodium hydroxide, magnesium oxide, or sodium acetate. If a base is used in the reaction mixture, the preferred mole ratio of reactants is 2 moles of the substituted aniline reagent for each mole of the compound of formula II.

If $X_1$ and $X_2$ are hydrogen then no further steps are necessary. Conventional alkylating, nitrosylating, sulfonating or halogenating agents can be used to form the $X_1$ and $X_2$ moieties. The X and $X_2$ moieties can be attached at any point throughout the synthesis. For example, the compound of formula IV can be reacted with an excess of a halogenating system for aromatic rings in the presence of a solvent at a temperature between about 15°–35° C. Halogenating systems are art recognized and include $SO_2CL_2$, $SOCl_2$, $Cl_2$, $Br_2$, $SOBr_2$, and $SO_2Br_2$. Solvents which can be used include acetic acid, chloroform, methylene chloride, 1 2-dichloroethane, other halogenated hydrocarbons containing at least one C—H bond, trifluoroacetic acid, methanesulfonic acid, and other organic acids. Preferably, an excess of up to 50 mole percent of the halogenating system is used to form the final product having the formula depicted in Formula I. If a haloalkyl substituent is desired as a moiety then this substituent can be provided on the starting material of formula II.

A method of synthesis can use a starting material of the formula:

-continued

Starting materials can be prepared by reacting 4-chloro resorcinol with ortho-carboxybenzene sulfonic acid, preferably in the presence of heat and polyphosphoric acid for about five hours at a temperature of about 155° C. The product can be purified using the techniques discussed above.

(V)

The remaining species of desired starting materials can be prepared from the compound of Formula V by protecting the hydroxyl groups which are to remain as hydroxyl groups, and chlorinating or alkylating the unprotected hydroxyl groups with a chlorinating or alkylating agent.

High Intensity Light Protective Compositions

The high intensity light protective compositions of this invention contain an effective amount of a substituted xanthene compound and a polymeric compound. The high intensity light includes intense light emitted by arc lamps, flash tubes, or lasers. An effective amount is that amount necessary or sufficient to absorb a significant amount of high intensity light at desired wavelengths. Preferably, the amount of substituted xanthene compound is in the range of about 0.001 to about 1.0 percent based upon the weight of the polymeric compound. The substituted xanthene compound is a compound having a xanthene core which is capable of effectively absorbing high intensity light, e.g. light emitted by lasers. The preferred substituted xanthene compounds used in the high intensity light protective compositions are those of formula I above and the preferred high intensity light is laser light.

The term polymeric compound is intended to encompass both inorganic polymers, organic polymers and resins. Inorganic polymers can include glass or glass like material or crystalline material capable of functioning in an optical device.

Organic polymers and resins can include plastics. The plastics can be thermoplastic or thermosetting plastics. Examples of types of organic polymers include polycarbonates, polyolefins, polyesters, aromatic polyamides, polyurethanes, aromatic polyurethanes, acrylic, polyacrylates, and esterified cellulosics. More specifically such organic polymers include polymethylmethacrylate, polyvinylchloride and polypropylene, and polycarbonate, particularly LEXAN 141, 141L, 161, 5184 and 181, preferably LEXAN 141L.

The LEXAN polycarbonates are of the type sold by General Electric, Schenectady, N.Y. and are particularly preferred polycarbonates. LEXAN polycarbonates typically have a haze of less than about 1% at a thickness of 0.125 inches, a specific gravity of 1.2, and a viscosity midpoint (melt flow rate) in the range of about 5.3 to about 16.5 g/10 minutes.

The preferred plastics of this invention are the polycarbonates. Polycarbonates of this invention preferably have the general formula $[OC_6H_4C(CH_3)_2C_6H_4)C)]_x$ and can be substituted along the polymeric chain with moieties which do not significantly affect the properties of the plastic. The polycarbonates of this invention have X values that give molecular weights in the range of about 10,000 to about 200,000. polycarbonates can be formed by reacting a bisphenol compound with phosgene. Conventional techniques can be used to prepare the polycarbonates such as interfacial polycondensation, homogeneous polycondensation, or transesterification.

Examples of other polycarbonate resins which are useful in this invention are described in U.S. Pat. No. 4,816,504, the contents of which are hereby incorporated by reference.

The high intensity light protective composition preferably further comprises a solubilizer. The solubilizer is used in an amount necessary or sufficient to solubilize the substituted xanthene compound. Preferably, the solubilizer is used in an amount in the range of about 0.001 to about 1.0% by weight. The solubilizer is an agent capable of molecularly dispersing the substituted xanthene compound in the polymeric compound leaving an optically clear material not having dispersed solids visible to the eye. An optically clear material is a material having a haze of less than about 2%.

The preferred solubilizers of the high intensity light protective compositions are surface active quaternary ammonium compounds, more preferably quaternary ammonium salts, particularly halogen salts such as chlorides. The surface active quaternary ammonium compound is preferably selected from the group consisting of trimethyldodecylammonium chloride, trimethylhexadecylammonium chloride, trimethyloctadecylammonium chloride, trimethylcocoammonium chloride, trimethylsoyammonium chloride, dimethylalkylbenzylammonium chloride, dimethyldicocoammonium chloride, dimethyldi(hydrogenated-tallow)ammonium chloride, N,N,N',N'-pentamethyl-N-tallow 1,3-propanediammonium dichloride, methylbis(2-hydroxyethyl)coco ammonium chloride, methylpolyoxyethylene(15)cocoammonium chloride, methylbis(2-hydroxyethyl)oleylammonium chloride, methylpolyoxyethylene(15)oleylammonium chloride, methylbis(2-hydroxyethyl)octadecylammonium chloride, methylpolyoxyethylene(15)octadecylammonium chloride, and dimethyldioctadecylammonium chloride. The most preferred surface active quaternary ammonium compound being dimethyldioctadecylammonium chloride.

The high intensity light protective composition is in a form capable of being manufactured, directly or indirectly, into high intensity light protective equipment. Examples of such forms include pellets or powder. When in pellet form, the substituted xanthene material is incorporated into pellets of the polymeric compound using conventional techniques, e.g. extrusion. When in powder form, the composition can be prepared by grinding or millinq, or the like.

Material which Prevents Transmission of High Intensity Light at Wavelengths between 482–556 Nanometers This invention also relates to material which prevents the transmission of high intensity light at a wavelength between about 482 to about 556 nanometers. The term prevent is intended to mean blocking at least 90% of the light at the selected wavelength, preferably 99.00 to 99.9999%, most preferably 99.99 to about 99.9999%. The material carries an effective amount of a substituted xanthene compound. An effective amount is that amount necessary or sufficient for preventing a substantial amount (about 90% or more), preferably 99% most preferably 99.99 to 99.9999%, of light at the desired wavelength from transmitting through the material. Preferably, the substituted xanthene compound is present in an amount in the range of 0.001–1% by weight of material. The amount of substituted xanthene compound may vary depending on the thickness of the material and on the substituted xanthene compound selected. Less absorber can be used in thicker materials while still obtaining the required amount of light absorption.

The substituted xanthene compound has a xanthene core and is capable of absorbing light at the wavelength desired to be blocked. The preferred substituted xanthene compound used to prevent the transmission of high intensity light are those of formula I.

The material of this invention is preferably used to prevent the transmission of laser light emitted from a Nd:YAG, Krypton or Argon laser. These lasers emit light at wavelengths of 532, 531, 514, and 488 nanometers, respectively. More preferably the laser light being blocked is of a wavelength of 532 nanometers corresponding to the Nd:YAG laser.

The substituted xanthene compound carried by the material is selected depending on the wavelength of light desired to be blocked. Table II below lists absorber compounds along with the particular wavelength of light they are capable of blocking. The absorbers of Table II correspond to the absorbers set forth in Table I.

TABLE II

| Absorber | Wavelength of Maximum Absorption in Methanol (Nanometers) | Estimated Wavelength of Maximum Absorption in Polycarbonate (Nanometers) |
|---|---|---|
| 1 | 529 | 523 |
| 2 | 538 | 532 |
| 3 | 538 | 532 |
| 4 | 542 | 536 |
| 5 | 543 | 537 |
| 6 | 544 | 538 |
| 7 | 529 | 523 |
| 8 | 537 | 531 |
| 9 | 555 | 549 |
| 10 | 528 | 522 |
| 11 | 488 | 482 |
| 12 | 562 | 556 |
| 13 | 529 | 523 |
| 14 | 529 | 523 |
| 15 | 528 | 522 |
| 16 | 545 | 539 |
| 17 | 529 | 523 |
| 18 | 548 | 542 |
| 19 | 517 | 511 |

Figure 1:
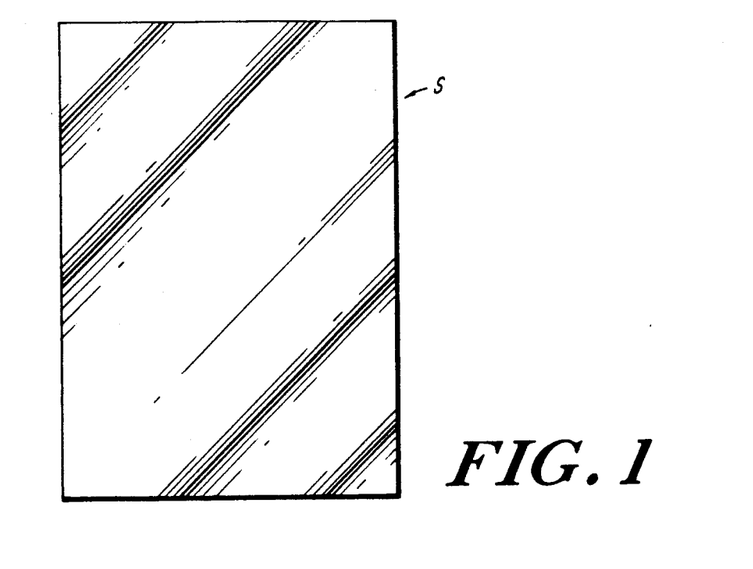
FIG. 1 is a schematic of a shield made of the material of the present invention.
Figure 2A:
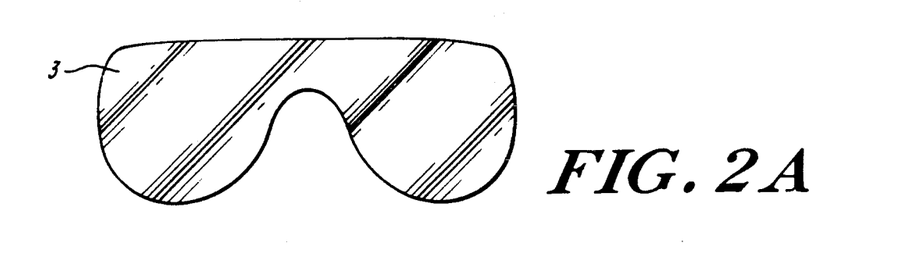
FIGS. 2A and 2B depict eyewear formed from the material of the present invention.
Figure 2B:
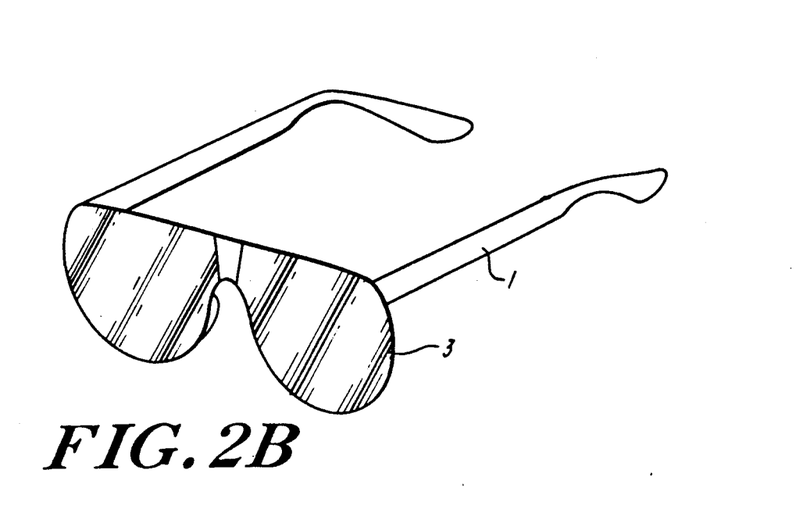

The term material is intended to include materials useful for high intensity light protective purposes. The materials can be any material capable of being formed into high intensity light protective equipment, e.g. lenses for eyewear such as goggles or glasses, optical filters, or shields for people or as components for optical instruments. The material can be formed into a sheet S as shown in FIG. 1 or can be formed into lenses for goggles as shown in FIGS. 2A or 2B. Preferably, the goggles have a frame 1 made of plastic or the like and lenses 3 made of the material of this invention. The term lenses is intended to encompass material capable of transmitting light and can be corrective or non-corrective lenses. The material can also be formed into a face shield for a mask type device. The material is preferably a polymeric compound as defined above.

The material can be formed into high intensity high protective equipment such as lenses for eyewear and shields using conventional techniques, e.q. injection molding, die stamping, casting, extrusion, film forming, and the like.

In an injection molding process, a hot thermoplast containing the substituted xanthene compound is injected into a mold. The granular plastic or pelletized plastic material containing the substituted xanthene compound is placed in a hopper and fed into a heated chamber located in front of a plunger or piston. The plunger or piston forces the heated plastic through the heated chamber, then through a nozzle into a sprue in the front half of a mold and on through the runners into the mold cavities. Injection molding processes can be conducted at pressures up to about 25,000 psi and temperatures of up to about 300° C. Nearly all thermoplasts are, or can be, molded using an injection molding process. This is the preferred process of the present invention.

Films and coatings of the plastic containing the substituted xanthene compounds can be produced using known processes. Films generally have thicknesses of 0.2-50 mm and can be flexible. Common methods of film forming include calendering, casting, extrusion, and dip, knife, or rollcoating. These processes are art recognized and are described in McGraw-Hill Encyclopedia of Science and Technology, Volume 10, 1971, pp 471-475, the contents of which are hereby incorporated by reference.

Method for Solubilizing an Absorber

This invention also relates to methods for solubilizing an absorber compound by contacting or mixing the absorber with an effective amount of a surface active quaternary ammonium compound. An effective amount is that amount necessary or sufficient to solubilize the absorber in a solvent. The absorber is considered to be solubilized when the solvent is optically clear as defined earlier. Preferably, the solubilizer is used in an amount in the range of about 0.001 to about 1% by weight.

For purposes of this invention the term absorber is intended to include dyes. Dyes are those compounds capable of imparting a color. The dyes can be aromatic compounds such as substituted and unsubstituted xanthene, fluorescein, rhodamine, anthraquinones, cyanines, merocyanines, squarylium or porphyrin compounds.

The solvent can be a solvent in which the solubilizer is soluble. The solvent is preferable an organic solvent such as organic polymers or resins including polycarbonates, polyolefins, polyesters, aromatic polyamides, polyurethanes, aromatic polyurethanes, acrylic, polyacrylates, and esterified cellulosics. More specifically such organic polymers include polymethylmethacrylate, polyvinylchloride, polypropylene, and polycarbonate, particularly LEXAN 141, 141L, 161, 5184 and 181, preferably LEXAN 141L.

The LEXAN polycarbonates are of the type sold by General Electric, Schenectady, N.Y. and are particularly preferred polycarbonates. LEXAN polycarbonates have a haze of less than about 1% at a thickness of 0.125 inches, a specific gravity of 1.2, and a viscosity midpoint (melt flow rate) in the range of about 5.3 to about 16.5 g/10 minutes.

The preferred plastics of this invention are the polycarbonates. Polycarbonates of this invention preferably have the general formula $[OC_6H_4C(CH_3)_2C_6H_4OCO]_x$ and can be substituted along the polymeric chain with moieties which do not significantly affect the properties of the plastic. The polycarbonates of this invention have X values that give molecular weights in the range of about 10,000 to about 200,000. Polycarbonates can be formed by reacting a bisphenol compound with phosgene. Conventional techniques can be used to prepare the polycarbonates such as interfacial polycondensation, homogeneous polycondensation, or transesterification.

Examples of other polycarbonate resins which are useful in this invention are described in U.S. Pat. No. 4,816,504, the contents of which are hereby incorporated by reference.

Surface active quaternary ammonium compounds which can be used in this method include trimethyldodecylammonium chloride, trimethylhexadecylammonium chloride, trimethyloctadecyl-ammonium chloride, trimethylcocoammonium chloride, trimethylsoyammonium chloride, dimethylalkylbenzylammonium chloride, dimethyldicocoammonium chloride, dimethyldi(hydrogenated tallow)ammonium chloride, N,N,N',N'-pentamethyl N-tallow-1,3-propanediammonium dichloride, methylbis(2-hydroxyethyl)cocoammonium chloride, methylpolyoxyethylene(15)cocoammonium chloride, methylbis(2-hydroxyethyl)oleylammonium chloride, methylpolyoxyethylene(15)oleylammonium chloride, methylbis(2-hydroxyethyl)octadecylammonium chloride, methylpolyoxyethylene(15)octadecylammonium chloride, and dimethyldioctadecylammonium chloride. The most preferred surface active quaternary ammonium compound being dimethyldioctadecylammonium chloride.

Properties of the Material

Materials used to make the high intensity light protective equipment and devices of this invention, e.g. plastics, typically have to comply with certain standards in order to be commercially valuable The materials of this invention containing the substituted xanthene compounds have some desirable properties which aid them in complying with these standards. For plastics which are going to be used in an injection molding process to form lenses for goggles or glasses, for example, the material should be capable of withstanding temperatures of up to 300° C. for up to ten minutes, preferably up to fifteen minutes without being substantially chemically modified. The materials of this invention are capable of withstanding temperatures such as these for this time period.

Another standard which is important for plastics used in high intensity light protective equipment, in accordance with this invention, is that the plastic be capable of withstanding up to 60 hours in a Weatherometer according to the American Society for Testing Materials (ASTM) standards at an optical density of 4.0 or above without having a substantial loss of ability to absorb light or being chemically modified. The ability to absorb light is dependent upon resistance to being chemically modified upon exposure to high intensity light.

A Weatherometer is a cylindrical chamber containing arc lighting on the internal surface. The plastic being tested is placed within the Weatherometer. The Weatherometer used to test the light stability of the materials of the present invention has a filtered xenon lamp to simulate the solar spectrum and can be run at 1120 watts per square meter. The test procedure is as follows:

| | |
|---|---|
| Radiant Exposure | 1120 W/$m_2$ Constant |
| Temperature | 120° F., Constant |
| Humidity | Ambient |
| Duration | 60 hours |
| | 20 hours on, 4 hours off |

The degradation is related to the total integrated exposure and interruptions in the test are not significant. The optical density of the plastic is measured before and after being placed in the Weatherometer. A change in the optical density is indicative of a change in the plastic's chemical composition and ability to absorb light.

Polycarbonates containing a substituted xanthene compound of this invention were capable of withstanding 60 hours in the above described Weatherometer and even further capable of withstanding up to 80 hours in the Weatherometer with no substantial change in chemical composition and ability to absorb light.

Another property used to evaluate the effectiveness of a plastic for laser protective purposes is optical clarity. To determine the optical clarity, the "haze" of a plastic is measured. The haze of the plastic should typically be less than 6% and preferably less than 4%, most preferably less than 2% with an optical density of 4. The haze can be measured using a Gardner hazemeter. Specimens are cut from the plastic and placed in the hazemeter. The specimen is illuminated by a substantially unidirectional beam and the incident light ($T_1$), the total light transmitted by the specimen ($T_2$), the light scattered by instrument ($T_3$), and the light scattered by the instrument and specimen are measured ($T_4$). The diffuse luminous transmittance ($T_d$) is calculated based on the formula below:

$$T_d = \frac{T_4 - T_3\left(\frac{T_2}{T_1}\right)}{T_1}$$

The haze is calculated as a percent using the following formula:

$$\text{Haze percent} = \frac{T_d}{T_t} \times 100$$

The $T_t$ is the total luminous transmittance which is equal to $T_2/T_1$.

The haze is that percentage of transmitted light which in passing through the specimen deviates from the incident beam by forward scattering. For the purpose of this invention, only light flux deviating more than 2.5° on the average is considered to be haze. The materials of the present invention containing substituted xanthene compounds have a haze of less than 2% with an optical density of 4.

A further advantage of the high intensity light protective compositions containing the solubilizer is that they provide desirable transmission properties based upon a sharpness of absorption band, i.e. the compositions can exclude light at a wavelength of 532 nm, while transmitting more light at other wavelengths. This is desirable when using such compositions for eyewear.

Quenching of Fluorescence in a Material With Phosphotungstic or Phosphomolybdic Acid

This invention also pertains to a method for quenching fluorescence in a material by introducing an effective amount of phosphotungstic or phosphomolybdic acid into the material. The phosphotungstic or phosphomolybdic acid also may enhance the thermal stability of the material. Thermal stability is defined as ability to resist chemical change when exposed to heat, e.g. temperatures of up to 300° C., for times in excess of three minutes and not more than about fifteen minutes. An effective amount for quenching fluorescence is that amount capable of eliminating or significantly reducing fluorescence and preferably is in the range of about 0.0001 to about 1 percent by weight of material.

An absorber is as defined earlier and includes dyes. A dye is a compound capable of imparting a color. Examples of dyes include aromatic dyes such as unsubstituted and substituted xanthene, cyanines merocyanines, rhodamines, squarylium, porphyrin, anthraquinones, and fluorescein compounds.

If the absorber is a cation, the absorber can be prepared as a phosphotungstic or phosphomolybdic acid salt, or as an admixture or in association with the phosphotungstic or phosphomolybdic acid. The absorber can be prepared as an association complex with phosphotungstic or phosphomolybdic acid if the absorber is neutral or anionic. The absorber can be mixed with phosphotungstic or phosphomolybdic acids using physical means.

This invention will be better understood from the following non-limiting examples.

EXAMPLE 1 PREPARATION OF ABSORBER NO. 2

A mixture of 14.5 grams (0.12 mole) of 2,6-dimethylaniline and 4.1 grams (0.01 mole) of dichlorosulfofloran were heated at reflux (215° C.) until the reaction was complete, approximately three hours. The reaction was tested for completeness using thin layer chromatography. A $SiO_2$ plate was run in 15% methanol in methylene chloride. The heating of the reaction mixture was continued until the unwanted orange spot on the thin layer chromatography plate disappeared, usually not more than five hours total heating time. After cooling, the solid was removed from the flask by repeated triturations with ether, filtering off the solid in the process. The solid was stirred for four hours in 500 ml. of ether and filtered. After drying, the solid was stirred in near boiling 15% HCl for approximately thirty minutes. The solution was filtered and subsequently dried to obtain compound A. At this stage, the purity of the product(A) was determined based upon thin layer chromatography analysis and the extinction coefficient of the product.

Absorber No. 2

The compound(A) (5.8 g., 0.01 mole) was suspended in 50 ml. of acetic acid and 3 g. (0.022 mole) of sulfuryl chloride in 10 ml. of acetic acid was added to the suspension while rapidly stirring. After two hours, 0.6 g. of sulfuryl chloride was added and the stirring was continued for approximately thirty minutes. The mixture was filtered, washed with 50 ml. of acetic acid, 200 ml. of ether, and dried to obtain absorber 2 as listed in Tables I and II.

EXAMPLE 2 PREPARATION OF ABSORBER NO. 3

A solution of 3.2 g. (0.005 mole) of Absorber 2 and 3.6 g. (0.00125 mole) of phosphotungstic acid (PTA) was prepared by dissolving Absorber No. 2 in 70 ml. of warmed methanol and adding to it a solution of PTA in 10 ml. of methanol. The solution was evaporated to dryness in a rotary evaporator under vacuum (aspirator) with heat. The solid, Absorber No. 3, was removed from the flask via trituration with ether and dried.

EXAMPLE 3 PREPARATION OF ABSORBER NO. 2 —CONCENTRATED POLYCARBONATE PELLETS

Absorber 2 (13.0 g) is thoroughly mixed with 13.0 g of dimethyl dioctadecyl ammonium chloride (Arquad 218 of the type sold by Akzo, Inc., Chicago, Ill.). 25.4 g of this mixture is added to 10 lbs. of polycarbonate (PC) pellets (LEXAN 5184 of the type sold by General Electric, Schenectady, N.Y.). The resulting mixture is tumbled for about fifteen minutes before being added to the feed hopper of an Anger twin screw extruder. The mixture is passed through the extruder and after cooling is chopped into highly colored PC pellets.

EXAMPLE 4 PREPARATION OF ABSORBER NO. 3 —CONCENTRATED POLYCARBONATE PELLETS

Absorber 3 (13.0 was thoroughly mixed with 13.0 g of dimethyl dioctadecyl ammonium chloride (Arquad 218 of the type sold by Akzo, Inc., Chicago, Ill ). 25.4 g of this mixture was added to 10 lbs. of polycarbonate (PC) pellets (LEXAN 5184 of the type sold by General Electric, Schenectady, N.Y.). The resulting mixture was tumbled for about fifteen minutes before adding to the feed hopper of an Anger twin screw extruder. The mixture was passed through the extruder and after cooling was chopped into highly colored PC pellets.

EXAMPLE 5 INJECTION MOLDING OF ABSORBER NO. 2/POLYCARBONATE PELLETS INTO LENSES

The concentrated PC/Absorber pellets (826g) formed in Example 3 are tumbled with 2806 g of uncolored PC pellets for approximately fifteen minutes. Subsequent to tumbling, the pellets are added to a feed hopper of a Kawaguchi Model JEKS-120V injection molding machine. The products molded are sun, wind, and dust protective lenses (SWIDS) These lenses were 3 mm thick and had an optical density of 4.4 at a wavelength of 532. The haze level of these lenses are measured with a Gardner hazemeter and is about 1.3%.

EXAMPLE 6 INJECTION MOLDING OF ABSORBER NO. 3/POLYCARBONATE PELLETS INTO LENSES

The concentrated PC/Absorber pellets (826 g) formed in Example 4 were tumbled with 2806 g of uncolored PC pellets for approximately fifteen minutes. Subsequent to tumbling, the pellets were added to a feed hopper of a Kawaguchi Model JEKS-120V injection molding machine. The products molded were sun, wind, and dust protective lenses (SWIDS) These lenses were 3 mm thick and had an optical density of 4.4 at a wavelength of 532. The haze level of these lenses were measured with a Gardner hazemeter and was 1.3%.

EXAMPLE 7 PREPARATION OF ABSORBER NO. 2/POLYCARBONATE PELLETS WITH AN INCREASED AMOUNT OF ABSORBER NO. 2

Example 3 is repeated except 40.8 g of a 50/50 by weight mixture of Absorber No. 2 and dimethyl dioctadecyl ammonium chloride (Arquad 218) is mixed with 10 lbs of PC pellets. The mixture is passed through a twin screw extruder and chopped into pellets. The Absorber No. 2/PC pellets (432 g) are mixed with 3200 g of uncolored PC pellets and injection molded into SWIDS in accordance with Example 5. The resulting SWIDS had an optical density of 4.4 at 532 nanometers and a haze level of about 1.5%.

EXAMPLE 8 PREPARATION OF ABSORBER NO. 3/POLYCARBONATE PELLETS WITH AN INCREASED AMOUNT OF ABSORBER NO. 3

This example was repeated in accordance with Example 4 except 40.8 g of a 50/50 by weight mixture of Absorber No. 3 and dimethyl dioctadecyl- ammonium chloride (Arquad 218) was mixed with 10 lbs of PC pellets. The mixture was passed through a twin screw extruder and chopped into pellets. The Absorber No. 3/PC pellets (432 g) were mixed with 3200 g of uncolored PC pellets and injection molded into SWIDS in accordance with Example 6. The resulting SWIDS had an optical density of 4.4 at 532 nanometers and a haze level of 1.5%.

EXAMPLE 9 DEMONSTRATION OF SOLUBILIZING EFFECT OF A SURFACE ACTIVE QUATERNARY AMMONIUM COMPOUND ON ABSORBER NO. 2

The following example demonstrates the solubilizing effect of dimethyl dioctadecyl-ammonium chloride (Arquad 218) on Absorber No. 2 in polycarbonate resin (LEXAN 141L of the type sold by General Electric, Schenectady, N.Y.). This example is conducted in a Haake Buchler System 40 polymer mixing device.

In a first test sample procedure, Absorber No. 2 (16 mg) is added to approximately 50–60 g. of polycarbonate (LEXAN 141L of the type sold by General Electric having a specific gravity of 1.2, a viscosity midpoint (melt flow rate) of 11.5 g/10 minutes, and a haze of about 1% at a thickness of 0.125 inches)) at a temperature of 265°–289° C. and mixed at 200 RPM for three minutes. The mixer is stopped, opened and the product is sampled and examined visually-. The polycarbonate is relatively uncolored with visible particles of absorber distributed throughout.

In a second test sample procedure in accordance with this invention, 32 mg. of Absorber No. 2 and 14 mg. of dimethyl dioctadecyl ammonium chloride (Arquad 218) are added to 50–60 g. of polycarbonate (LEXAN 141L, General Electric) at a temperature of 265°–275° C. and mixed at 200 RPM for two minutes. The product from this experiment is highly- colored and appeared clear with no visible particles of absorber demonstrating the solubilizing effect of the quaternary ammonium compound.

EXAMPLE 10 DEMONSTRATION OF SOLUBILIZING EFFECT OF A SURFACE ACTIVE QUATERNARY AMMONIUM COMPOUND ON ABSORBER NO. 3

The following example demonstrates the solubilizing effect of dimethyl dioctadecyl ammonium chloride (Arquad- 218) on Absorber No. 3 in polycarbonate resin (LEXAN 141L, General Electric, Schenectady, N.Y.). This example was conducted in a Haake Buchler System 40 polymer mixing device.

In a first test sample procedure, Absorber No. 3 (16 mq) was added to approximately 50-60 g. of polycarbonate (LEXAN 141L, General Electric) at a temperature of 265°-289° C. and mixed at 200 RPM for three minutes. The mixer was stopped, opened and the product was sampled and examined visually. The polycarbonate was relatively uncolored with visible particles of absorber distributed throughout.

In a second test sample procedure in accordance with this invention, 32 mg. of Absorber No. 3 and 14 mg. of dimethyl dioctadecyl ammonium chloride (Arquad 218) was added to 50-60 q. of polycarbonate (LEXAN 141L of the type sold by General Electric) at a temperature of 265°-275° C. and mixed at 200 RPM for two minutes. The product from this experiment was highly colored and appeared clear with no visible particles of absorber demonstrating the solubilizing effect of the quaternary ammonium compound.

EXAMPLES 11-37

When Example 3 is repeated in a series of Examples 11-40 using the absorbers of Table I in each Example as follows:

| Example | Absorber |
| --- | --- |
| 11 | 1 |
| 12 | 4 |
| 13 | 5 |
| 14 | 6 |
| 15 | 7 |
| 16 | 8 |
| 17 | 9 |
| 18 | 10 |
| 19 | 11 |
| 20 | 12 |
| 21 | 13 |
| 22 | 14 |
| 23 | 15 |
| 24 | 16 |
| 25 | 17 |
| 26 | 18 |
| 27 | 19 |
| 28 | 20 |
| 29 | 21 |
| 30 | 22 |
| 31 | 23 |
| 32 | 24 |
| 33 | 25 |
| 34 | 26 |
| 35 | 27 |
| 36 | 28 |
| 37 | 29 |

PC pellets containing each of the absorbers are obtained. Each of the separate batches of pellets obtained from Examples 11-40 are formed into lenses in accordance with Examples 5 and 8 to form 3 mm thick lenses containing the respective Absorbers of Table 1. The lenses so formed from the materials of Examples 11-41 each have an optical density of 4.4 at a wavelength indicated for each absorber in Table II where wavelengths are indicated in Table II and a haze in the range of less than 2.0g.

Those skilled in the art will be able to ascertain, using no more than routine experimentation, many equivalents of the specific embodiments of the invention described herein.

These and all other equivalents are intended to be encompassed by the following claims.

We claim:

1. A substituted xanthene compound of the formula:

wherein $R_1$-$R_6$ are each independently alkyl, alkenyl, alkynyl, halogen, haloalkyl, $SO_2N(alkyl)_2$, aryl, substituted aryl, or hydrogen;

$Y_1$ and $Y_2$ are each independently alkyl, alkenyl, alkynyl, or hydrogen;

$X_1$, $X_2$, $X_3$, and $X_4$ are each independently selected from the group consisting of hydrogen, halogen, haloalkyl, alkyl, alkenyl, alkynyl, $NO_2$, SO, $SO_2N(alkyl)_2$, and $SO_2$ groups; and A is selected from the group consisting of $SO_3$, $SO_2N(alkyl)_2$, $CO_2$, and $CO_2CH_3$, whereby at least two of the $R_1R_6$ moieties are not hydrogen and $R_3$ or $R_4$ can optionally form a phenyl ring with $R_5$ or $R_1$ or $R_2$ can optionally form a phenyl ring with $R_6$.

2. A substituted xanthene compound as claimed in claim 1 wherein $R_1$-$R_6$, $Y_1$ and $Y_2$ are each independently lower alkyl groups or hydrogen.

3. A substituted xanthene compound as claimed in claim 1 or 2 wherein the lower alkyl groups are methyl, ethyl, or propyl.

4. A substitued xanthene compound as claimed in claim 3 wherein the lower alkyl group is methyl.

5. A substituted xanthene compound as claimed in claim 1 wherein $X_1$ and $X_2$, are each independently selected from the group consisting of Cl, F, I, Br, and $CF_3$ and $X_3$ and $X_4$ are hydrogen.

6. A substituted xanthene compound as claimed in claim 5 wherein $X_1$ and $X_2$ are the same.

7. A substituted xanthene compound as claimed in claim 6 wherein $X_1$ and $X_2$ are Cl.

8. A substituted xanthene compound as claimed in claim 1 wherein the R, Y, and X moieties are positioned such that the compound is optically symmetrical.

9. A substituted xanthene compound as claimed in claim 8 wherein $R_1$, $R_2$, $R_3$, and $R_4$ are located in the 2 and 6 positions of the phenyl rings.

10. A substituted xanthene compound as claimed in claim 8 wherein $R_1$, $R_2$, $R_3$, and $R_4$ are located in the 3 and 5 positions of the phenyl rings.

11. A substituted xanthene compound as claimed in claim 8 or 10 wherein $R_1$ and $R_3$ are homologous and $R_2$ and $R_4$ are homologous.

12. A substituted xanthene compound as claimed in claim 11 wherein $R_1$ and $R_3$ are the same and $R_2$ and $R_4$ are the same.

13. A substituted xanthene compound as claimed in claim 1 wherein $X_1$ and $X_2$ are Cl; $R_1$, $R_2$, $R_3$, $R_4$ are each methyl groups; and the remaining R, X, and Y moieties are hydrogen.

14. A compound as claimed in claim 13 having the following formula:

* * * * *